(12) United States Patent
Takai et al.

(10) Patent No.: US 7,732,627 B2
(45) Date of Patent: Jun. 8, 2010

(54) HIGH-PURITY CYCLOALIPHATIC DIEPOXY COMPOUND AND PREPARATION PROCESS THEREOF

(75) Inventors: Hideyuki Takai, Otake (JP); Hiroto Tanigawa, Otake (JP); Katsuya Maruo, Otake (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 11/792,782

(22) PCT Filed: Dec. 27, 2005

(86) PCT No.: PCT/JP2005/023916

§ 371 (c)(1),
(2), (4) Date: Jun. 11, 2007

(87) PCT Pub. No.: WO2006/073093

PCT Pub. Date: Jul. 13, 2006

(65) Prior Publication Data

US 2008/0045729 A1  Feb. 21, 2008

(30) Foreign Application Priority Data

Jan. 7, 2005 (JP) ............................. 2005-003175

(51) Int. Cl.
*C07D 301/14* (2006.01)
(52) U.S. Cl. ...................... 549/525; 549/547
(58) Field of Classification Search ............... 549/525, 549/547
See application file for complete search history.

(56) References Cited

U.S. PATENT DOCUMENTS

| | | | |
|---|---|---|---|
| 3,075,955 A | 1/1963 | Starcher et al. | |
| 4,002,669 A | 1/1977 | Gross et al. | |
| 2003/0059618 A1 | 3/2003 | Takai | |
| 2004/0242839 A1 | 12/2004 | Takai | |

FOREIGN PATENT DOCUMENTS

| | | |
|---|---|---|
| EP | 0 090 239 A1 | 10/1983 |
| EP | 0 844 262 A2 | 5/1998 |
| EP | 1 389 615 A1 | 2/2004 |
| JP | 48-29899 | 4/1973 |
| JP | 48-89999 A | 11/1973 |
| JP | 58-172387 | 10/1983 |
| JP | 2002-275169 A | 9/2002 |
| JP | 2003-13001 A | 1/2003 |
| JP | 2004-285125 A | 10/2004 |
| JP | 2005-248135 A2 | 9/2005 |
| WO | WO-2005/090325 A1 | 9/2005 |

*Primary Examiner*—Janet L Andres
*Assistant Examiner*—David E Gallis
(74) *Attorney, Agent, or Firm*—Birch, Stewart, Kolasch & Birch, LLP (57) ABSTRACT

A high-purity cycloaliphatic diepoxy compound of General Formula (II) is an epoxidized product of a cycloaliphatic diolefinic compound of General Formula (I) having an isomer content as detected in gas chromatography (GC) of 15% or less:

[Chemical Formula 1]

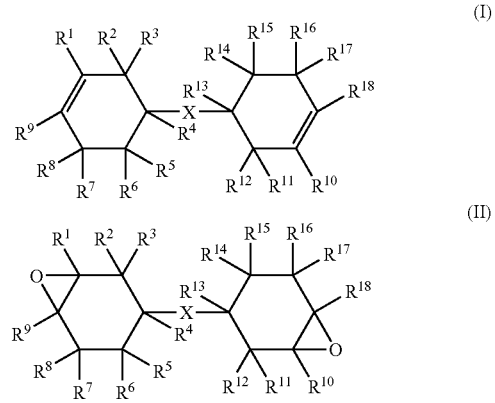

wherein X represents a bivalent group selected from the group consisting of, for example, O, S, —SO—, —SO$_2$—, —CH$_2$—, and —C(CH$_3$)$_2$—; and R$^1$ to R$^{18}$ may be the same as or different from each other and each represent hydrogen atom, a halogen atom, a hydrocarbon group which may contain oxygen atom or a halogen atom, or an alkoxy group which may be substituted. Such a high-purity cycloaliphatic diepoxy compound is prepared by producing the cycloaliphatic diolefinic compound through distillation, epoxidizing the compound with an aliphatic percarboxylic acid containing substantially no water, carrying out desolvation, and further purifying the epoxidized compound through distillation.

16 Claims, 6 Drawing Sheets

HIGH-PURITY CYCLOALIPHATIC DIEPOXY COMPOUND AND PREPARATION PROCESS THEREOF

TECHNICAL FIELD

The present invention relates to a high-purity cycloaliphatic diepoxy compound prepared by oxidizing a cycloaliphatic diolefinic compound with an aliphatic percarboxylic acid containing substantially no water, and purifying the oxidized compound, and to a process for preparing the same. More specifically, it relates to a high-purity cycloaliphatic diepoxy compound as a product from a diolefin which includes a compound having a 3,3'-cyclohexenyl skeleton represented by following General Formula (I):

[Chemical Formula 1]

(I)

and has a content of other structural isomers of 15% or less. It also relates to a process for preparing the cycloaliphatic diepoxy compound through purification by distillation. Such cycloaliphatic diepoxy compounds are useful in applications requiring thermal stability and/or optical transparency, such as coatings, inks, adhesives, sealants, stabilizers, insulating materials, and display materials such as liquid crystals.

BACKGROUND ART

A variety of diepoxy compounds each having two cycloaliphatic skeletons per molecule are currently commercially available as, for example, CEL-2021 (3,4-epoxycyclohexylmethyl 3',4'-epoxycyclohexanecarboxylate), CEL-3000 (1,2,8,9-diepoxylimonene), and CEL-2081 (a ∈-caprolactone oligomer combined with 3,4-epoxycyclohexylmethanol and 3,4-epoxycyclohexanecarboxylic acid at both ends through ester bond, respectively), each of which is available from Daicel Chemical Industries, Ltd. CEL-3000 contains methyl group in carbon constituting epoxy group and thereby has a lower reactivity of epoxy group than compounds which do not contain such methyl group. CEL-2021P and CEL-2081 are hydrolyzable, because they have ester bond in the molecule. Accordingly, cured products of them may have impaired properties when used at high temperatures and high humidity or used under such a condition that a strong acid is formed. Demands have therefore been made to provide epoxy compounds having a cycloaliphatic skeleton with no ester bond in the molecule.

Japanese Unexamined Patent Application Publication (JP-A) No. 48-29899 discloses a cured article of a cycloaliphatic diepoxy compound obtained by synthetically preparing a diepoxy compound represented by following compound (II):

[Chemical Formula 2]

(II)

wherein X is $CH_2$; and $R^1$ to $R^{18}$ are each hydrogen atom, and carrying out a curing reaction of this compound with an acid anhydride. The document mentions that the resulting cured article has improved properties as compared with cured articles of known cycloaliphatic diepoxy compounds. This technique, however, uses perbenzoic acid for the preparation of the cycloaliphatic diepoxy compound and is hard to use industrially. Japanese Unexamined Patent Application Publication (JP-A) No. 58-172387 discloses a technique of synthetically preparing a percarboxylic acid from hydrogen peroxide, an acid catalyst, and an organic acid, extracting the percarboxylic acid with an organic solvent, and carrying out epoxidation of the extracted compound. This technique employs long procedures, yields large amounts of waste materials, and requires complicated operations. In addition, the percarboxylic acid contains not only water but also hydrogen peroxide and the acid catalyst, even though in trace amounts, and may thereby become unstable and be reduced in concentration in a short time in the reaction step for the preparation of the percarboxylic acid and extraction step. The reduction in concentration of the percarboxylic acid also causes oxygen formation, and formed oxygen makes inside of the reactor dangerous and invites side reactions of the epoxidized product typically in the epoxidation reaction step and a step of purifying the resulting epoxy compound. Such by-products reduce the recovery of the target product and contaminate the preparation apparatus. Thus, the technique is industrially disadvantageous.

Japanese Unexamined Patent Application Publication (JP-A) No. 2002-275169 discloses a technique of synthetically preparing a cycloaliphatic diepoxy compound represented by General Formula (II) by oxidizing acetaldehyde with air to yield peracetic acid, and epoxidizing a compound having two cycloaliphatic olefin skeletons and containing no ester bond in the molecule with the peracetic acid. However, only desolvation is conduced in the synthetic preparation of the cycloaliphatic diepoxy compound, and the product contains high-molecular weight components having shorter elution times than that of the cycloaliphatic diepoxy compound detected in gel permeation chromatography (hereinafter referred to as "GPC") analysis; impurities having shorter retention times than that of the cycloaliphatic diepoxy compound represented by General Formula (II), as well as reaction intermediates, as detected in analysis using a gas chromatograph (hereinafter referred to as "GC"). The product is insufficient in color (APHA) and insufficient for use in display materials, such as liquid crystals, requiring thermal stability and/or optical transparency.

Patent Document 1: Japanese Unexamined Patent Application Publication (JP-A) No. 48-29899
Patent Document 2: Japanese Unexamined Patent Application Publication (JP-A) No. 58-172387
Patent Document 3: Japanese Unexamined Patent Application Publication (JP-A) No. 2002-275169

DISCLOSURE OF INVENTION

Problems to be Solved by the Invention

An object of the present invention is to provide a high-purity cycloaliphatic diepoxy compound prepared by epoxidizing a specific cycloaliphatic diolefinic compound, and a process for preparing the same.

Means for Solving the Problems

The present inventors have succeeded to prepare a cycloaliphatic diepoxy compound having a higher purity by carrying out epoxidation of a compound having two cycloaliphatic olefin skeletons and having a low content of structural isomers with an aliphatic percarboxylic acid containing substantially no water, and purifying the epoxidized compound through distillation.

Specifically, according to a first embodiment of the present invention, there is provided a high-purity cycloaliphatic diepoxy compound represented by following General Formula (II), as an epoxidized product of a cycloaliphatic diolefinic compound being represented by following General Formula (I) and having an isomer content detected in gas chromatography (GC) of 15% or less:

[Chemical Formula 3]

wherein X represents a bivalent group selected from the group consisting of oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$ to R$^{18}$ may be the same as or different from each other and each represent hydrogen atom, a halogen atom, a hydrocarbon group which may contain oxygen atom or a halogen atom, or an alkoxy group which may be substituted.

According to a second embodiment of the present invention, there is provided a high-purity cycloaliphatic diepoxy compound according to the first embodiment, in which the isomer includes at least one of the following compounds:

[Chemical Formula 4]

wherein X represents a bivalent group selected from the group consisting of oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$ to R$^{18}$ may be the same as or different from each other and each represent hydrogen atom, a halogen atom, a hydrocarbon group which may contain oxygen atom or a halogen atom, or an alkoxy group which may be substituted.

There is also provided, according to a third embodiment of the present invention, the high-purity cycloaliphatic diepoxy compound according to first or second embodiment, in which the cycloaliphatic diepoxy compound has a concentration of high-molecular weight components detected in gel permeation chromatography (hereinafter referred to as GPC) analysis of 5.5% or less, the high-molecular weight components eluting earlier than the cycloaliphatic epoxy compound represented by following General Formula (II) in GPC analysis:

[Chemical Formula 5]

wherein X represents a bivalent group selected from the group consisting of oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$ to R$^{18}$ may be the same as or different from each other and each represent hydrogen atom, a halogen atom, a hydrocarbon group which may contain oxygen atom or a halogen atom, or an alkoxy group which may be substituted.

According to a fourth embodiment of the present invention, there is provided a high-purity cycloaliphatic diepoxy compound according to any one of first, second, and third embodiments in which the cycloaliphatic diepoxy compound has a concentration of impurities detected in GC analysis of 19.5% or less, the impurities having retention times shorter than that of the cycloaliphatic epoxy compound General Formula (II) in GC analysis.

According to a fifth embodiment of the present invention, there is provided a high-purity cycloaliphatic diepoxy compound according to any one of the first, second, third, and fourth embodiments, in which the cycloaliphatic diepoxy compound has a concentration of a reaction intermediate represented by following General Formula (III) and detected in GC analysis of 4.5% or less:

[Chemical Formula 6]

(III)

wherein X represents a bivalent group selected from the group consisting of oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$ to R$^{18}$ may be the same as or different from each other and each represent hydrogen atom, a halogen atom, a hydrocarbon group which may contain oxygen atom or a halogen atom, or an alkoxy group which may be substituted.

According to a sixth embodiment of the present invention, there is provided a high-purity cycloaliphatic diepoxy compound according to any one of the first, second, third, fourth, and fifth embodiments, in which the cycloaliphatic diepoxy compound has color (APHA) of 60 or less.

According to a seventh embodiment of the present invention, there is provided a high-purity cycloaliphatic diepoxy compound according to any one of the first, second, third, fourth, fifth, and sixth embodiments, as an epoxidized product with an aliphatic percarboxylic acid containing substantially no water.

According to an eighth embodiment of the present invention, there is provided a process for preparing a high-purity cycloaliphatic diepoxy compound represented by following General Formula (II), the process including the steps of purifying a cycloaliphatic diolefinic compound represented by following General Formula (I) through distillation, epoxidizing the purified cycloaliphatic diolefinic compound with an aliphatic percarboxylic acid containing substantially no water, carrying out desolvation of the epoxidized compound, and further purifying the epoxidized compound through distillation:

[Chemical Formula 7]

(I)

-continued (II)

wherein X represents a bivalent group selected from the group consisting of oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$ to R$^{18}$ may be the same as or different from each other and each represent hydrogen atom, a halogen atom, a hydrocarbon group which may contain oxygen atom or a halogen atom, or an alkoxy group which may be substituted.

According to a ninth embodiment of the present invention, there is provided a process for preparing a high-purity cycloaliphatic diepoxy compound according to the eighth embodiment, in which the concentration of a reaction intermediate represented by following General Formula (III) and detected in GC analysis is 4.5% or less:

[Chemical Formula 8]

(III)

wherein X represents a bivalent group selected from the group consisting of oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$ to R$^{18}$ may be the same as or different from each other and each represent hydrogen atom, a halogen atom, a hydrocarbon group which may contain oxygen atom or a halogen atom, or an alkoxy group which may be substituted.

According to a tenth embodiment of the present invention, there is provided a process for preparing a high-purity cycloaliphatic diepoxy compound according to one of the eighth or ninth embodiment, further including preparing the aliphatic percarboxylic acid through oxidation of a corresponding aldehyde with oxygen.

According to an eleventh embodiment of the present invention, there is provided a process for preparing a high-purity cycloaliphatic diepoxy compound according to any one of the eighth, ninth, and tenth embodiments, in which the aliphatic percarboxylic acid has a water content of 0.8 percent by weight or less.

According to a twelfth embodiment of the present invention, there is provided a process for preparing a high-purity cycloaliphatic diepoxy compound according to any one of the eighth, ninth, tenth, and eleventh embodiments, in which the aliphatic percarboxylic acid is peracetic acid.

According to a thirteenth embodiment of the present invention, there is provided a process for preparing a high-purity cycloaliphatic diepoxy compound according to any one of the eighth, ninth, tenth, eleventh, and twelfth embodiments, in which the purification through distillation is carried out at a heating temperature of 100° C. to 350° C. and a pressure of 50 to 0.01 Torr.

ADVANTAGES

According to the present invention, there are provided high-purity cycloaliphatic diepoxy compounds. Cured articles obtained from these compounds are excellent in thermal stability and optical transparency and are advantageously used in display materials such as liquid crystals.

BEST MODE FOR CARRYING OUT THE INVENTION

The present invention will be illustrated in detail below.

A high-purity cycloaliphatic diepoxy compound represented by General Formula (II) according to the present invention is prepared by carrying out epoxy-oxidation of a cycloaliphatic diolefinic compound represented by General Formula (I) with an aliphatic percarboxylic acid containing substantially no water, and subjecting the epoxidized compound to distillation. The cycloaliphatic diolefinic compound has reduced contents typically of the five isomers.

The purification through distillation for reducing isomers is carried out by placing the material typically in a simple distillation apparatus according to a batch system or in a distillation apparatus including a thin-film evaporator such as wiped film evaporator (WFE) or falling film evaporator (FFE), or a molecular still, or a distillation column, and carrying out distillation under following conditions. Each of these apparatuses can be used alone or in combination. The purification through distillation is carried out under conditions at a pressure of 50 to 0.01 Torr, preferably 20 to 0.03 Torr, and more preferably 10 to 0.05 Torr, and a heating temperature of 100° C. to 350° C., preferably 120° C. to 330° C., and more preferably 150° C. to 300° C.

The isomers remain at the bottom of the column, and the cycloaliphatic diolefinic compound represented by General Formula (I) distills as overhead of the column. The structures of the isomers can be identified, for example, NMR, GC-MS, and GC-IR.

A cycloaliphatic diolefinic compound represented by General Formula (I), used as a raw material, is generally synthetically prepared by dehydration of a corresponding compound having hydroxyl group. The cycloaliphatic diolefinic compound can be prepared, for example, by a process of synthesizing from a compound having a cyclohexanol structure, as described in Japanese Unexamined Patent Application Publication (JP-A) No. 48-29899, JP-A No. 58-172387, and JP-A No. 2000-169399. With reference to General Formula (I), the resulting cycloaliphatic diolefinic compound has double bonds at the 3- and 4-positions with respect to the bivalent group X. The compound having hydroxyl group for use as a raw material for the cycloaliphatic diolefinic compound is preferably one having hydroxyl group at the 4-position with respect to the bivalent group X. While broadly further including compounds each having two or more cyclohexane rings combined with hydroxyl group per molecule, which are starting materials not corresponding to General Formula (I), examples of these compounds include hydrogenated biphenols, dicyclohexanolmethane, bis(dimethylcyclohexanol) methane, 1,2-bis(cyclohexanol)ethane, 1,3-bis(cyclohexanol)propane, 1,4-bis(cyclohexanol)butane, 1,5-bis (cyclohexanol)pentane, 1,6-bis(cyclohexanol)hexane, 2,2-bis(cyclohexanol)propane, bis(cyclohexanol) phenylmethane, α,(α-bis(4-hydroxycyclohexyl)-4-(4-hydroxy-α,α-dimethylcyclohexylmethyl)-ethylbenzene, 3,3-bis(cyclohexanol)pentane, 5,5-bis(cyclohexanol)heptane, dodecahydrofluorenediol, tris(cyclohexanol)methane, tris(cyclohexanol)ethane, 1,3,3-tris(cyclohexanol)butane, tetrakis(cyclohexanol)ethane, 2,2-bis[4,4'-bis(cyclohexanol) cyclohexyl]propane, hydrogenated bisphenol C (C: cyclohexane), hydrogenated polyphenols, and mixtures of these compounds.

Olefinic compounds prepared from such starting compounds not corresponding to General Formula (I), and epoxy compounds derived therefrom can also be prepared in the same manner as in the present invention.

An aliphatic percarboxylic acid containing substantially no water is preferably used as an epoxidizing agent in epoxidation of the double bonds of a cycloaliphatic diolefinic compound represented by General Formula (I). This is because a ring-opening reaction of epoxy group proceeds, and the yield of the epoxy compound is reduced if an epoxidation reaction is carried out in the presence of water. Thus, the aliphatic percarboxylic acid contains substantially no water (is substantially free from water). Specifically, the water content of the aliphatic percarboxylic acid is 0.8 percent by weight or less, and preferably 0.6 percent by weight or less. The term "aliphatic percarboxylic acid containing substantially no water" used herein refers to, for example, peracetic acid prepared by oxidizing acetaldehyde with air. By taking peracetic acid as an example, it may be prepared according to a process described typically in German Unexamined Patent Application Publication (DE-A) No. 1418465 or Japanese Unexamined Patent Application Publication (JP-A) No. 54-3006. According to this process, an aliphatic percarboxylic acid can be substantially inexpensively obtained, because it can be continuously synthetically prepared in a larger amount in a higher concentration than the preparation of an aliphatic percarboxylic acid by synthesizing the aliphatic percarboxylic acid from hydrogen peroxide and extracting the aliphatic percarboxylic acid with a solvent.

Examples of aliphatic percarboxylic acids for use herein include performic acid, peracetic acid, perisobutyric acid, and trifluoroperacetic acid. Among them, peracetic acid is a preferred epoxidizing agent, because it is industrially inexpensively available and is highly stable. The amount of an aliphatic percarboxylic acid as an epoxidizing agent is not strictly limited, and an optimum amount in each case is determined depending typically on variable factors such as the epoxidizing agent to be used, the desired degree of epoxidation, and the cycloaliphatic diolefinic compound represented by General Formula (I) used as a starting material. When the target compound is a compound having a large number of epoxy groups per molecule, the epoxidizing agent is preferably used in an equivalent mole or more relative to olefin groups. However, use of the epoxidizing agent in an amount exceeding 2 times by mole is generally disadvantageous in view of economical efficiency and side reactions mentioned below. Accordingly, when the epoxidizing agent is peracetic acid, the amount is preferably 1 to 1.5 times by mole.

Epoxidation is carried out while determining whether or not an inert solvent is used and adjusting the reaction temperature depending on the apparatus to be used and the properties of starting material. The inert solvent can be used in order to reduce the viscosity of starting material and stabilize the epoxidizing agent as a result of dilution. When the epoxidizing agent is peracetic acid, aromatic compounds and esters, for example, can be used. Among them, hexane, cyclohexane, toluene, ethyl acetate, and methyl acetate are preferred as solvents. The amount of such solvents is 10 to 500 parts by weight, and preferably 50 to 300 parts by weight, relative to the olefin. If the amount is less than 10 parts by weight, a side reaction may be often caused by an oxidizing agent such as acetic acid. If the amount exceeds 500 parts by weight, it may take much time to complete the reaction, or the yield per volume may be reduced.

Reaction temperatures herein are determined depending on the reactivity of an epoxidizing agent to be used. The reaction is carried out at temperatures of generally 0° C. or higher and 100° C. or lower. With respect to peracetic acid as a preferred epoxidizing agent, the reaction temperature is preferably 20° C. to 70° C. If the reaction is carried out at a temperature of 20° C. or lower, the reaction may proceed slowly. If the reaction is carried out at a temperature of 70° C., peracetic acid may decompose. The molar ratio of the epoxidizing agent to unsaturated bonds in the cycloaliphatic diolefinic compound represented by General Formula (I) is 1/1 to 1/3, and preferably 1/1.1 to 1/2. An extra procedure for treating a reaction mixture is not required. For example, it is enough to stir the reaction mixture typically for one to five hours. The epoxidized product can be isolated by a suitable procedure. For example, it can be isolated by precipitating in a poor solvent, by placing the reaction mixture into hot water with stirring, and removing the solvent through distillation, or by direct desolvation.

The cycloaliphatic diepoxy compound represented by General Formula (II) obtained by these procedures, however, is insufficient in color and still contains residual high-molecular weight components detected in GPC analysis, and impurities and/or reaction intermediates having shorter retention times than that of the cycloaliphatic diepoxy compound represented by General Formula (II) in GC analysis.

Examples of high-molecular weight components detected in GPC analysis include polymers of the cycloaliphatic diepoxy compound represented by General Formula (II), and mono- and poly-adducts of the cycloaliphatic diepoxy compound with a carboxylic acid by-produced from the epoxidizing agent.

While broadly indicating inclusive of compounds not corresponding to General Formula (II), examples of mono-adducts of the cycloaliphatic diepoxy compound with a carboxylic acid by-produced from the epoxidizing agent include 3-hydroxy-4-acetoxy-3',4'-epoxybicyclohexane, 1-acetoxy-2-hydroxy-1',2'-epoxy-4,4'-methylenedicyclohexane, 1-acetoxy-2-hydroxy-2,2',6,6'-tetramethyl-1',2'-epoxy-4,4'-methylenedicyclohexane, 1-acetoxy-2-hydroxy-1',2'-epoxy-4,4'-ethylenedicyclohexane, 1-acetoxy-2-hydroxy-1',2'-epoxy-4,4'-(propane-1,3-diyl)dicyclohexane, 1-acetoxy-2-hydroxy-1',2'-epoxy-4,4'-(butane-1,4-diyl)dicyclohexane, 1-acetoxy-2-hydroxy-1',2'-epoxy-4,4'-(pentane-1,5-diyl)dicyclohexane, 1-acetoxy-2-hydroxy-1',2'-epoxy-4,4'-(hexane-1,6-diyl)dicyclohexane, 2-(3-hydroxy-4-acetoxycyclohexyl)-2-(3,4-epoxycyclohexyl)propane, 1-acetoxy-2-hydroxy-1',2'-epoxy-4,4'-(phenylmethylene)dicyclohexane, α,α-bis(3,4-epoxycyclohexyl)-4-((3-hydroxy-4-acetoxy-α,α-dimethylcyclohexyl)methyl)ethylbenzene, 3-(3-hydroxy-4-acetoxycyclohexyl)-3-(3,4-epoxycyclohexyl)pentane, 3-(3-hydroxy-4-acetoxycyclohexyl)-3-(3,4-epoxycyclohexyl)heptane, 2-hydroxy-3-acetoxy-6,7-epoxydodecahydrofluorene, (3-hydroxy-4-acetoxycyclohexyl)-bis(3,4-epoxycyclohexyl)methane, 1-(3-hydroxy-4-acetoxycyclohexyl)-2,2-bis(3,4-epoxycyclohexyl)ethane, 1-(3-hydroxy-4-acetoxycyclohexyl)-3,3-bis(3,4-epoxycyclohexyl)ethane, 1-(3-hydroxy-4-acetoxycyclohexyl)-1,2,2-tris(3,4-epoxycyclohexyl)ethane, 2-(4-(3-hydroxy-4-acetoxycyclohexyl)cyclohexyl)-2-(4-(',4-epoxycyclohexyl)cyclohexyl)propane, and 2-(3-hydroxy-3-methyl-4-acetoxycyclohexyl)-2-(3-methyl-3,4-epoxycyclohexyl) propane.

While broadly indicating as above, examples of poly-adducts of the cycloaliphatic diepoxy compound with a carboxylic acid by-produced from the epoxidizing agent include 3,3'-dihydroxy-4,4'-diacetoxybicyclohexane, bis(3-hydroxy-4-acetoxycyclohexyl)methane, bis(3-hydroxy-3,5-dimethyl-4-acetoxycyclohexyl)methane, 1,2-bis(3-hydroxy-4-acetoxycyclohexyl)ethane, 1,3-bis(3-hydroxy-4-acetoxycyclohexyl)propane, 1,4-bis(3-hydroxy-4-acetoxycyclohexyl)butane, 1,5-bis(3-hydroxy-4-acetoxycyclohexyl)pentane, 1,6-bis(3-hydroxy-4-acetoxycyclohexyl)hexane, 2,2-bis(3-hydroxy-4-acetoxycyclohexyl)propane, bis(3-hydroxy-4-acetoxycyclohexyl)phenylmethane, α,α-bis(3-hydroxy-4-acetoxycyclohexyl)-4-((3-hydroxy-4-acetoxy-α,α-dimethylcyclohexyl)methyl)ethylbenzene, 3,3-bis(3-hydroxy-4-acetoxycyclohexyl)pentane, 3,3-bis(3-hydroxy-4-acetoxycyclohexyl)heptane, 2,6-dihydroxy-3,7-diacetoxydodecahydrofluorene, tris(3-hydroxy-4-acetoxycyclohexyl)methane, 1,1,2-tris(3-hydroxy-4-acetoxycyclohexyl)ethane, 1,1,3-tris(3-hydroxy-4-acetoxycyclohexyl)butane, tetrakis(3-hydroxy-4-acetoxycyclohexyl)ethane, 2,2-bis[4,4'-bis(3-hydroxy-4- acetoxycyclohexyl)cyclohexyl]propane, and 2,2-bis(3-hydroxy-3-methyl-4-acetoxycyclohexyl)propane.

Examples of impurities being detected in GC analysis and having shorter retention times than that of the cycloaliphatic diepoxy compound represented by General Formula (II) include solvents used in the epoxidation reaction, such as hexane, cyclohexane, toluene, ethyl acetate, and methyl acetate; carboxylic acids by-produced from the epoxidizing agent, such as formic acid, acetic acid, isobutyric acid, and trifluoroacetic acid; compounds derived from solvents used in the synthetic preparation of the cycloaliphatic diolefinic compound represented by General Formula (I), such as naphthalene and tetramethylbenzene; olefin monool compounds by-produced in the synthetic preparation of the cycloaliphatic olefinic compound, and epoxidized products of such olefin monool compounds; monoolefinic compounds as by-produced impurities in the synthetic preparation of the cycloaliphatic diolefinic compound represented by General Formula (I), and epoxidized products of such monoolefinic compounds; and mono-adducts of the epoxidized products of such monoolefinic compounds with a carboxylic acid by-produced from the epoxidizing agent.

Examples of olefin monool compounds by-produced in the synthetic preparation of the cycloaliphatic olefinic compound represented by General Formula (I) include, while broadly indicating as above, 4-(3-cyclohexenyl)cyclohexanol, 4-(3-cyclohexenyl)methylcyclohexanol, 3,5-dimethyl-4-(3,5-dimethyl-3-cyclohexenyl)methylcyclohexanol, 4-(2-(3-cyclohexenyl)ethyl)cyclohexanol, 4-(3-(3-cyclohexenyl)propyl)cyclohexanol, 4-(4-(3-cyclohexenyl)butyl)cyclohexanol, 4-(4-(3-cyclohexenyl)pentyl)cyclohexanol, 4-(5-(3-cyclohexenyl)hexyl)cyclohexanol, 4-((1-(3-cyclohexenyl)-1-methyl)ethyl)cyclohexanol, 4-(3-cyclohexenylphenylmethyl)cyclohexanol, α,α-bis(3-cyclohexenyl)-4-(4-hydroxy-α,α-dimethylcyclohexylmethyl)ethylbenzene, 4-(1-(3-cyclohexenyl)-1-ethyl)propylcyclohexanol, 4-(1-(3-cyclohexenyl)-1-ethyl)pentylcyclohexanol, 2-hydroxy-[1,2,3,4,5,8,4a,4b,8a,8b]decahydrofluorene, 4-bis(3-cyclohexenyl)methylcyclohexanol, 4-bis(3-cyclohexenyl)ethylcyclohexanol, 4-bis(3-cyclohexenyl)butylcyclohexanol, 4-(1,2,2-tris(3-cyclohexenyl))ethylcyclohexanol, 4-(4-(4-(1-(3-cyclohexenyl)-1-methyl)ethylcyclohexyl)methylcyclohexyl)cyclohexanol, and 2-methyl-4-(1-(3-methyl-3-cyclohexenyl)-1-methyl)ethylcyclohexanol.

Examples of epoxidized products of such olefin monool compounds include, while broadly indicating as above, 4-(3,4-epoxycyclohexyl)cyclohexanol, 4-(3,4-epoxycyclohexylmethyl)cyclohexanol, 3,5-dimethyl-4-(3,5-dimethyl-3,4-epoxycyclohexylmethyl)cyclohexanol, 4-(2-(3,4-epoxycyclohexyl)ethyl)cyclohexanol, 4-(3-(3,4-epoxycyclohexyl)propyl)cyclohexanol, 4-(4-(3,4-epoxycyclohexyl)butyl)cyclohexanol, 4-(5-(3,4-epoxycyclohexyl)pentyl)cyclohexanol, 4-(6-(3,4-epoxycyclohexyl)hexyl)cyclohexanol, 4-(1-(3,4-epoxycyclohexyl)-1-methylethyl)cyclohexanol, 4-((3,4-epoxycyclohexylphenyl)methyl)cyclohexanol, α,α-bis(3,4-epoxycyclohexyl)-4-(4-hydroxy-α,α-dimethylcyclohexylmethyl)ethylbenzene, 4-(1-(3,4-epoxycyclohexyl)-1-ethylpropyl)cyclohexanol, 4-(1-(3,4-epoxycyclohexyl)-1-ethylpentyl)cyclohexanol, 2-hydroxy-[1,2,3,4,5,8,4a,4b,8a,8b]decahydrofluorene, 4-bis(3,4-epoxycyclohexyl)methylcyclohexanol, 4-bis(3,4-epoxycyclohexyl)ethylcyclohexanol, 4-bis(3,4-epoxycyclohexyl)butylcyclohexanol, 4-(1,2,2-tris(3,4-epoxycyclohexyl))ethylcyclohexanol, 4-(4-(1-(4-(3,4epoxycyclohexyl)cyclohexyl)-1-methyl)ethylcyclohexyl)cyclohexanol, and 2-methyl-4-(1-(3-methyl-3,4-epoxycyclohexyl)-1-methyl)ethylcyclohexanol.

Examples of monoolefinic compounds as by-produced impurities in the synthetic preparation of the cycloaliphatic diolefinic compound represented by General Formula (I) include, while broadly indicating as above, 4-cyclohexylcyclohexene, 4-(cyclohexylmethyl)cyclohexene, 2,6-dimethyl-4-(3,5-dimethylcyclohexylmethyl)cyclohexene, 1-(3-cyclohexenyl)-2-cyclohexylethane, 1-(3-cyclohexenyl)-3-cyclohexylpropane, 1-(3-cyclohexenyl)-4-cyclohexylbutane, 1-(3-cyclohexenyl)-5-cyclohexylpentane, 1-(3-cyclohexenyl)-6-cyclohexylhexane, 2-(3-cyclohexenyl)-2-cyclohexylpropane, 3-cyclohexenylcyclohexylphenylmethane, α,α-dicyclohexyl-4-(α,α-dimethyl-3-cyclohexenylmethyl)ethylbenzene, 3-(3-cyclohexenyl)-3-cyclohexylpentane, 3-(3-cyclohexenyl)-3-cyclohexylheptane, [1,2,3,4,5,8,4a,4b,8a,8b]decahydrofluorene, 4-(dicyclohexylmethyl)cyclohexene, 1-(3-cyclohexenyl)-2,2-dicyclohexylethane, 1-(3-cyclohexenyl)-3,3-dicyclohexylbutane, 1-(3-cyclohexenyl)-1,2,2-tricyclohexylethane, 2-(4-(3-cyclohexenyl)cyclohexyl)-2-bicyclohexylpropane, and 2-(3-methyl-3-cyclohexenyl)-2-(3-methylcyclohexyl)propane.

Examples of epoxidized products of monoolefinic compounds (iv) as impurities by-produced in the synthetic preparation of the cycloaliphatic diolefinic compound represented by General Formula (I) include, while broadly indicating as above, 1,2-epoxybicyclohexane, 1,2-epoxy-4,4'-methylenedicyclohexane, 1,2-epoxy-2,2',6,6'-tetramethyl-4,4'-methylenedicyclohexane, 1-(3,4-epoxycyclohexyl)-2-cyclohexylethane, 1-(3,4-epoxycyclohexyl)-3-cyclohexylpropane, 1-(3,4-epoxycyclohexyl)-4-cyclohexylbutane, 1-(3,4-epoxycyclohexyl)-5-cyclohexylpentane, 1-(3,4-epoxycyclohexyl)-6-cyclohexylhexane, 2-(3,4-epoxycyclohexyl)-2-cyclohexylpropane, (3,4-epoxycyclohexyl)cyclohexylphenylmethane, α,α-dicyclohexyl-4-(α,α-dimethyl-3,4-epoxycyclohexylmethyl)ethylbenzene, 3-(3,4-epoxycyclohexyl)-3-cyclohexylpentane, 3-(3,4-epoxycyclohexyl)-3-cyclohexylheptane, 2,3-epoxy-[1,2,3,4,5,8,4a,4b,8a,8b]decahydrofluorene, 4-(bis(3,4-epoxycyclohexyl)methyl)cyclohexene, 1-(3,4-epoxycyclohexyl)-2,2-biscyclohexylethane, 1-(3,4-epoxycyclohexyl)-3,3-biscyclohexylbutane, 1-(3,4-epoxycyclohexyl)-1,2,2-triscyclohexylethane, 2-(4-(3,4-epoxycyclohexyl)cyclohexyl)-2-bicyclohexylpropane, and 2-(3-methyl-3,4-epoxycyclohexyl)-2-(3-methylcyclohexyl)propane.

Examples of mono-adducts of the epoxidized products of such monoolefinic compounds as impurities by-produced in the synthetic preparation of the cycloaliphatic diolefinic compound represented by General Formula (I) with a carboxylic acid by-produced from the epoxidizing agent include, while broadly indicating as above, 1-acetoxy-2-hydroxybicyclohexane, 1-acetoxy-2-hydroxy-4-(cyclohexylmethyl)cyclohexane, 1-acetoxy-2-hydroxy-2,6-dimethyl-4-(3,5-dimethylcyclohexylmethyl)cyclohexane, 1-(3-hydroxy-4-acetoxycyclohexyl)-2-cyclohexylethane, 1-(3-hydroxy-4-acetoxycyclohexyl)-3-cyclohexylpropane, 1-(3-hydroxy-4-acetoxycyclohexyl)-4-cyclohexylbutane, 1-(3-hydroxy-4-acetoxycyclohexyl)-5-cyclohexylpentane, 1-(3-hydroxy-4-acetoxycyclohexyl)-6-cyclohexylhexane, 2-(3-hydroxy-4-acetoxycyclohexyl)-2-cyclohexylpropane, (3-hydroxy-4-acetoxycyclohexyl)cyclohexylphenylmethane, α,α-dicyclohexyl-4-(α,α-dimethyl-3-hydroxy-4-acetoxycyclohexylmethyl)ethylbenzene, 3-(3-hydroxy-4-acetoxycyclohexyl)-3-cyclohexylpentane, 3-(3-hydroxy-4-acetoxycyclohexyl)-3-cyclohexylheptane, 2-hydroxy-3- acetoxy-[1,2,3,4,5,8,4a,4b,8a,8b]decahydrofluorene, 4-(3-hydroxy-4-acetoxycyclohexyl)cyclohexene, 1-(3-hydroxy-4-acetoxycyclohexyl)-2,2-biscyclohexylethane, 1-(3-hydroxy-4-acetoxycyclohexyl)-3,3-biscyclohexylbutane, 1-(3-hydroxy-4-acetoxycyclohexyl)-1,2,2-triscyclohexylethane, 2-(4-(3-hydroxy-4-acetoxycyclohexyl)cyclohexyl)-2-bicyclohexylpropane, and 2-(3-methyl-3-hydroxy-4-acetoxycyclohexyl)-2-(3-methylcyclohexyl)propane.

The reaction intermediate detected in gas chromatograph analysis is a monoepoxymonoolefinic compound represented by General Formula (III), corresponding to the cycloaliphatic diolefinic compound represented by General Formula (I), except with one double bond being epoxidized. The monoepoxymonoolefinic compound is converted into a cycloaliphatic diepoxy compound represented by General Formula (II) as a result of epoxidation of the residual double bond.

After investigations on purification of the cycloaliphatic diepoxy compound represented by General Formula (II) prepared by the above procedure, the present inventors have found that high-molecular weight components, reaction intermediates, and compounds derived from impurities in the starting material, typified by the five isomers, can be further removed from the epoxidized product after desolvation by purification through distillation, and that this improves the color (hue) of a resin composition containing the cycloaliphatic diepoxy compound represented by General Formula (II), and a cured article thereof, such as a display material.

A process for the preparation of a high-purity cycloaliphatic diepoxy compound according to the present invention is a process of removing a solvent from an epoxidized product obtained in the above-mentioned step, and purifying the epoxidized product through distillation. This removes high-molecular weight components, reaction intermediates, and compounds derived from impurities in the starting material and yields a high-purity cycloaliphatic epoxy compound with good color. A high-purity cycloaliphatic diepoxy compound according to the present invention has a concentration of high-molecular weight components detected in GPC analysis of 5.5%, preferably 4.1% or less, and more preferably 2.5% or less; a concentration of impurities detected in GC analysis and having shorter retention times than that of the cycloaliphatic diepoxy compound represented by General Formula (II) of 19.5% or less, preferably 16.4% or less, and more preferably 1.7% or less; a concentration of reaction intermediates of 4.5% or less, preferably 3.5% or less, and more preferably 0.1% or less; and color (APHA) of 60 or less, preferably 40 or less, and more preferably 20 or less.

The purification through distillation after epoxidation reaction is carried out after removing a solvent (desolvation) from the reaction product. The desolvation is generally carried out using a simple distillation apparatus according to a batch system or a thin-film evaporator such as WFE or FFE under such conditions at a pressure of 300 to 30 Torr, preferably 200 to 50 Torr and a heating temperature of 50° C. to 180° C., and preferably 60° C. to 150° C.

After carrying out desolvation according to the above procedure under above conditions, the purification through distillation is conducted by placing the reaction product in a distillation apparatus including a simple distillation apparatus according to a batch system, a thin-film evaporator such as WFE or FFE, a molecular still, or a distillation column, and carrying out distillation under following conditions. Each of these apparatuses can be used alone or in combination. The purification through distillation after epoxidation is carried out under conditions at a pressure of 50 to 0.01 Torr, preferably 20 to 0.03 Torr, and more preferably 10 to 0.05 Torr, and a heating temperature of 100° C. to 350° C., preferably 120° C. to 330° C., and more preferably 150° C. to 300° C.

Cycloaliphatic diepoxy compounds represented by General Formula (II) purified through distillation are high-purity cycloaliphatic diepoxy compounds which have reduced concentrations of high-molecular weight components detected in GPC analysis, have low concentrations of reaction intermediates, and compounds derived from impurities in the starting material as above, detected in GC analysis, and have good color. The compounds can thereby yield various coatings, inks, adhesives, sealants, and molded articles by subjecting the compound to homopolymerization, copolymerization, or reaction with another compound. They can also be used as various intermediates for other uses using these compounds. Examples of end uses of the cycloaliphatic diepoxy compounds represented by General Formula (II) include acid removers, furniture coatings, ornament coatings, coatings for beverage cans and other cans, adhesives, undercoatings for automobiles, sealers, finish coatings, inks for alphabetic information or image information, sealants for electronic components, photoresists suitable for developing printing matrices or printed circuit boards, casting printing rolls, molded articles formed from molding compositions or sheet-forming compositions mainly containing unsaturated polyesters and polystyrenes, solvents, flame-retardants, pharmaceutical preparations and articles for medical use. The compounds can also be used as intermediates for the preparation of other compounds useful for these and other end uses. The cycloaliphatic diepoxy compounds represented by General Formula (II) can have thermal stability, optical transparency, and good dielectric properties, which are features of resins using compounds having cycloaliphatic skeletons. They are therefore advantageously used as liquid crystals and other display materials requiring thermal stability and optical transparency.

EXAMPLES

The present invention will be illustrated in further detail with reference to several examples below. It should be understood, however, these examples are not to be construed as limiting the scope of the present invention in any way.

<GPC Analysis>

In a pretreatment, 0.04 g of a cycloaliphatic diepoxy compound represented by General Formula (II), wherein X is —C(CH$_3$)$_2$—, and each of R$^1$ to R$^{18}$ is hydrogen (H), was dissolved in 2 g of tetrahydrofuran (hereinafter referred to as "THF") and filtrated through a filter having a pore size of 0.50 μm [DISMIC13JP050AN, Toyo Roshi Ltd.]. The solution of cycloaliphatic diepoxy compound in THF was analyzed by GPC, and proportions of peak areas of individual components were defined as the concentration of the individual components. A total of the concentrations of components eluting faster (earlier) than the cycloaliphatic diepoxy compound was determined by calculation as the concentration of high-molecular weight components.

Apparatus: HLC-8220GPC (Tosoh Corporation)

Detector: differential refractometer (RI detector)

Precolumn: TSKGUARDCOLUMN SUPER HZ-L 4.6 mm×20 mm

Column:

sample side, TSK-GEL SUPER HZM-N 4.6 mm×150 mm×four columns reference side, TSK-GEL SUPER HZM-N 6.0 mm×150 mm×one column and TSK-GEL SUPER H-RC 6.0 mm×150 mm
  Temperature of thermostat: 40° C.
  Moving bed: THF
  Flow rate of moving bed: 0.35 mL/min.
  Amount of sample: 114 μL
  Data sampling time: 10 minutes to 26 minutes after sample injection <Gas Chromatograph Analysis 1>

The cycloaliphatic epoxy compound was directly analyzed by gas chromatograph without pretreatment, and proportions of peak areas of individual components were defined as the concentrations of the individual components.
  Apparatus: Model GC14-B (Shimadzu Corporation)
  Column: Thermon3000/5% Shincarbon A 2.6 mm×3 m
  Temperature of thermostat: the thermostat was held at 60° C. for 2 minutes, raised in temperature at a rate of 10° C./min. to 250° C., and held at 250° C. for 19 minutes
  Injection port temperature: 250° C.
  Detector area temperature: 250° C.
  Detector: flame ionization detector (FID)

<Gas Chromatograph Analysis 2>
  Apparatus: HP-6890N (Hewlett Packard)
  Column: DB-FFAP (64) 0.25 mm in inner diameter×30 m in length
  Temperature of thermostat: the thermostat was held at 50° C. for 5 minutes, raised in temperature at a rate of 10° C./min. to 200° C., held at 200° C. for 5 minutes, raised in temperature at a rate of 10° C./min. to 230° C., and held at 230° C. for 25 minutes
  Injection port temperature: 230° C.
  Detector area temperature: 240° C.
  Detector: FID Synthesis Example 1

Synthesis of 2,2-bis(3'-cyclohexenyl)propane

In a 10-liter four-neck flask equipped with a stirrer, a 20-tray distillation column, and a thermometer were placed 6 kg (25.0 mol) of hydrogenated bisphenol-A and 490 g (3.6 mol) of potassium hydrogen sulfate (formula weight: 136.2), followed by heating to 140° C., to melt hydrogenated bisphenol-A. After melting, the mixture was further heated to 180° C. and stirring was started. Then, a reaction began gradually, and 505 ml (28 mol) of water distilled under normal pressure over four hours. The distilled water corresponds to 56% of the theoretical value.

Thereafter, the reaction system was reduced in pressure to 10 Torr at the same temperature, to distill water and 2,2-bis(3'-cyclohexenyl)propane from the overhead of the distillation column over five hours. The distilled water and 2,2-bis(3'-cyclohexenyl)propane were separated into two layers using a decanter, and 2,2-bis(3'-cyclohexenyl)propane as an upper layer was collected.

The reaction was completed at the time when distillation of water and 2,2-bis(3'-cyclohexenyl)propane stopped. The yield of a crude distillate of 2,2-bis(3'-cyclohexenyl)propane was 4880 g.

Next, 4800 g of the crude distillate was placed in a 5-liter four-neck flask equipped with a stirrer, a 20-stage distillation column, and a thermometer and was raised in temperature to 170° C. on an oil bath. The reaction system was reduced in pressure to 10 Torr (1.33 kPa) to distil water, and 2,2-bis(3'-cyclohexenyl)propane was rectified at a reflux ratio of 1 over five hours, while maintaining the temperature of the overhead of the distillation column at 160° C. Thus, a colorless transparent liquid was obtained.

Figure 1:
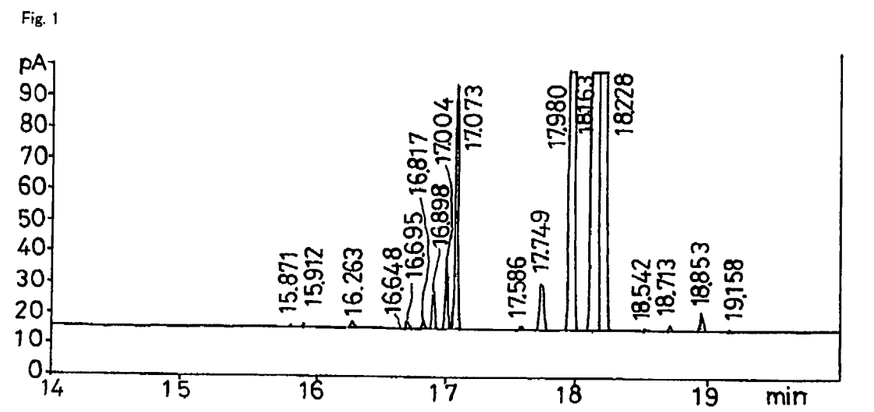
FIG. 1 is a chart in gas chromatograph analysis of 2,2-bis (3'-cyclohexenyl)propane prepared according to Synthesis Example 1.

The yield of the resulting 2,2-bis(3'-cyclohexenyl)propane was 4403 g. This compound had a purity determined by gas chromatograph (according to Gas Chromatograph Analysis 2) of 91.1%, an iodine number of 247 ($I_2$-g/100 g), and an APHA of 10 or less. The chart obtained in the gas chromatograph analysis is shown in FIG. 1. The purity was determined based on the areal percentage of a main peak observed at retention times of 17.9 minutes to 18.3 minutes.

Figure 5:
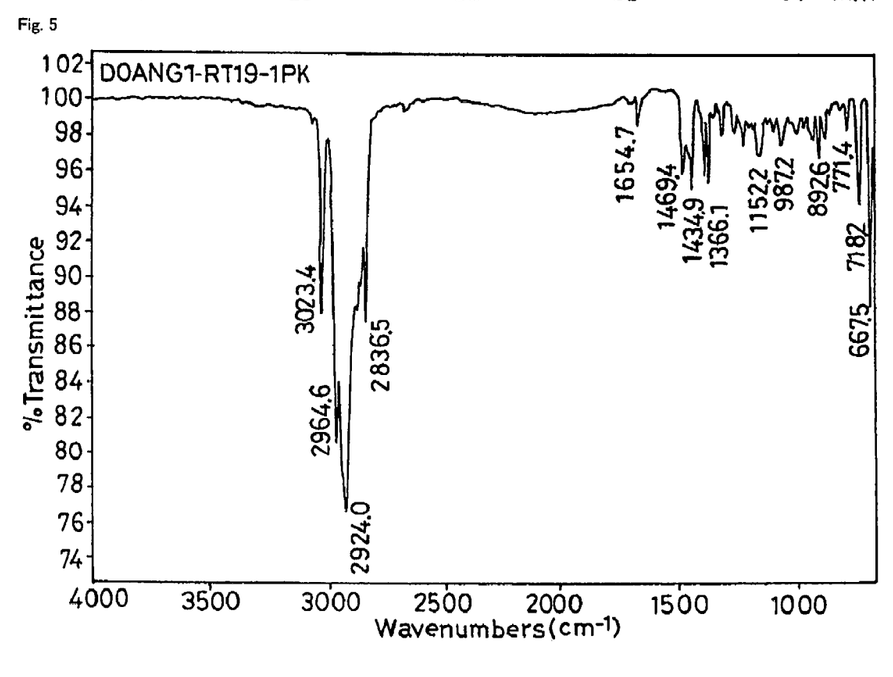
FIG. 5 is an IR chart of a peak at 17.9 minutes observed in 2,2-bis(3'-cyclohexenyl)propane prepared according to Synthesis Example 1.
Figure 6:
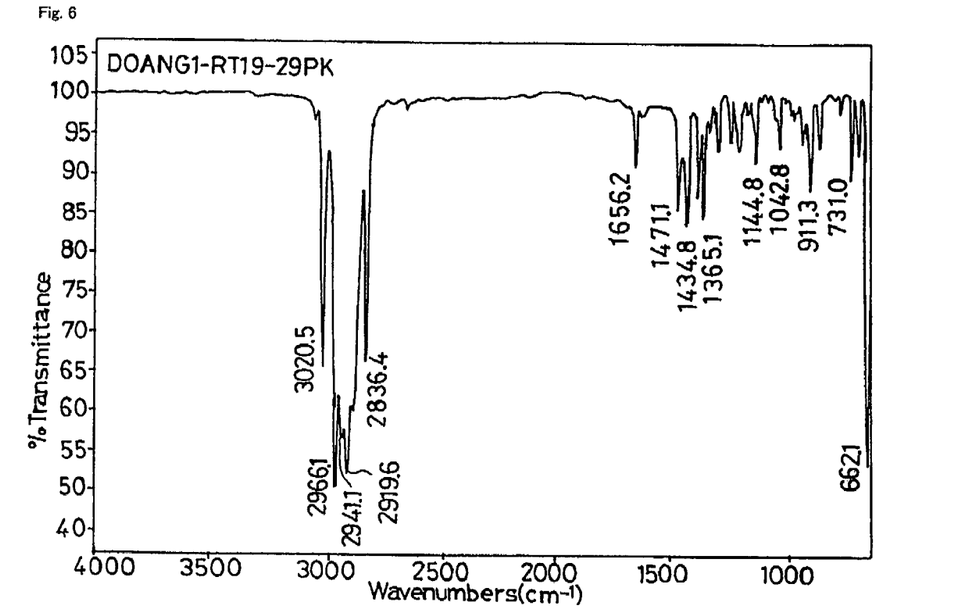
FIG. 6 is an IR chart of a peak at 18.1 minutes observed in 2,2-bis(3'-cyclohexenyl)propane prepared according to Synthesis Example 1.
Figure 7:
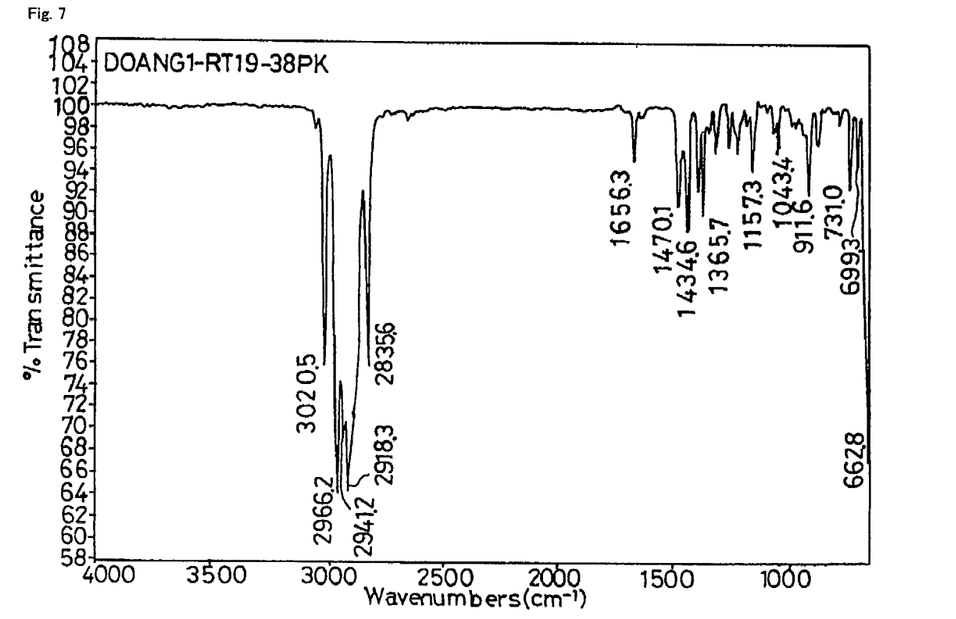
FIG. 7 is an IR chart of a peak at 18.2 minutes observed in 2,2-bis(3'-cyclohexenyl)propane prepared according to Synthesis Example 1.
Figure 8:
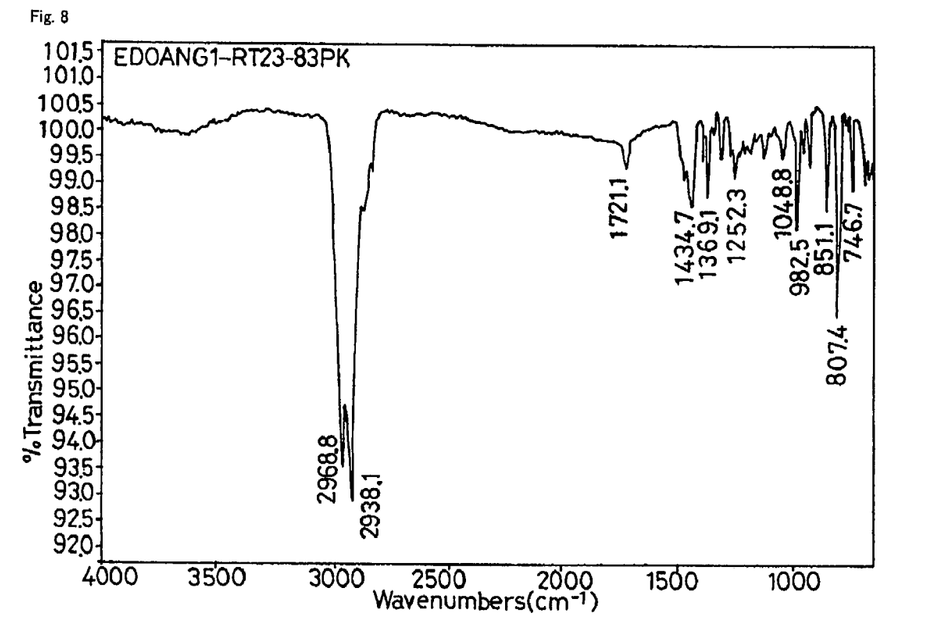
FIG. 8 is an IR chart of a peak at 30.1 minutes observed in the cycloaliphatic diepoxy compound prepared according to Example 1.
Figure 9:
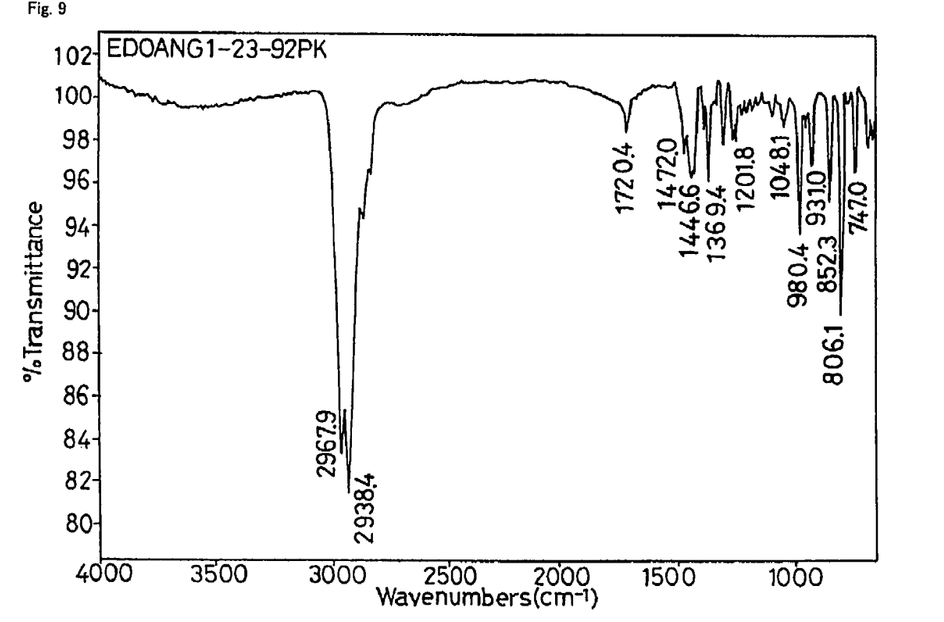
FIG. 9 is an IR chart of a peak at 30.2 minutes observed in the cycloaliphatic diepoxy compound prepared according to Example 1.
Figure 10:
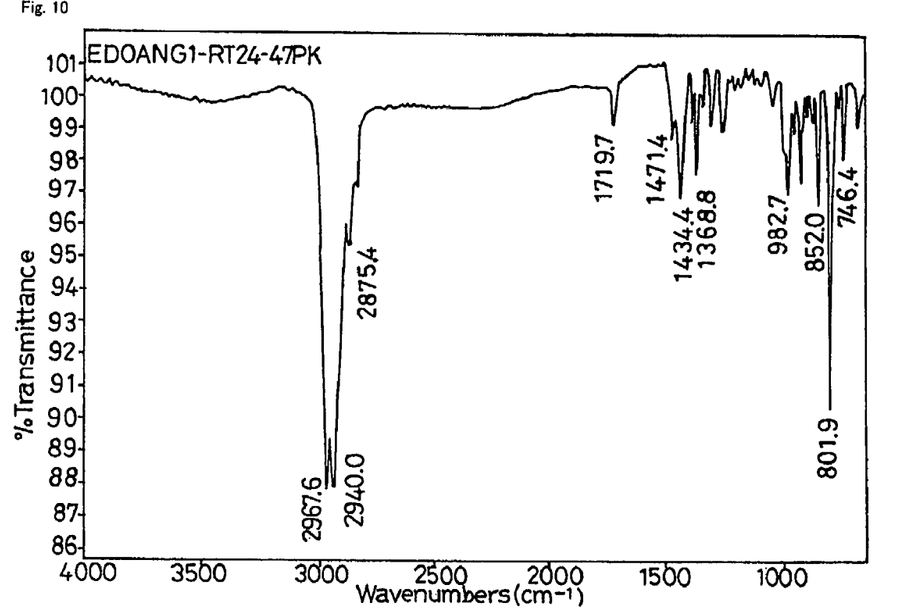
FIG. 10 is an IR chart of a peak at 30.6 minutes observed in the cycloaliphatic diepoxy compound prepared according to Example 1.
Figure 11:
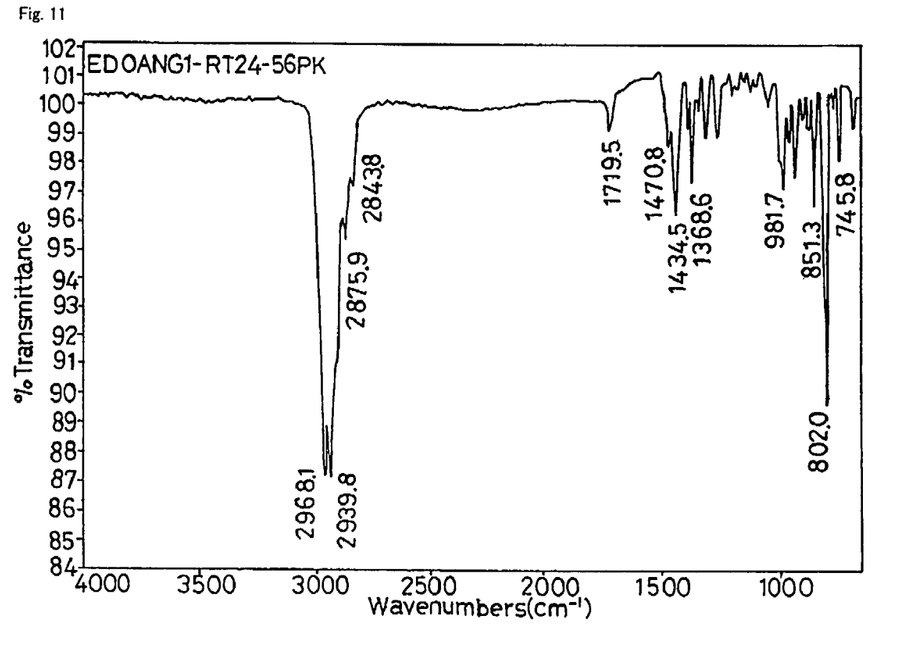
FIG. 11 is an IR chart of a peak at 30.7 minutes observed in the cycloaliphatic diepoxy compound prepared according to Example 1.
Figure 12:
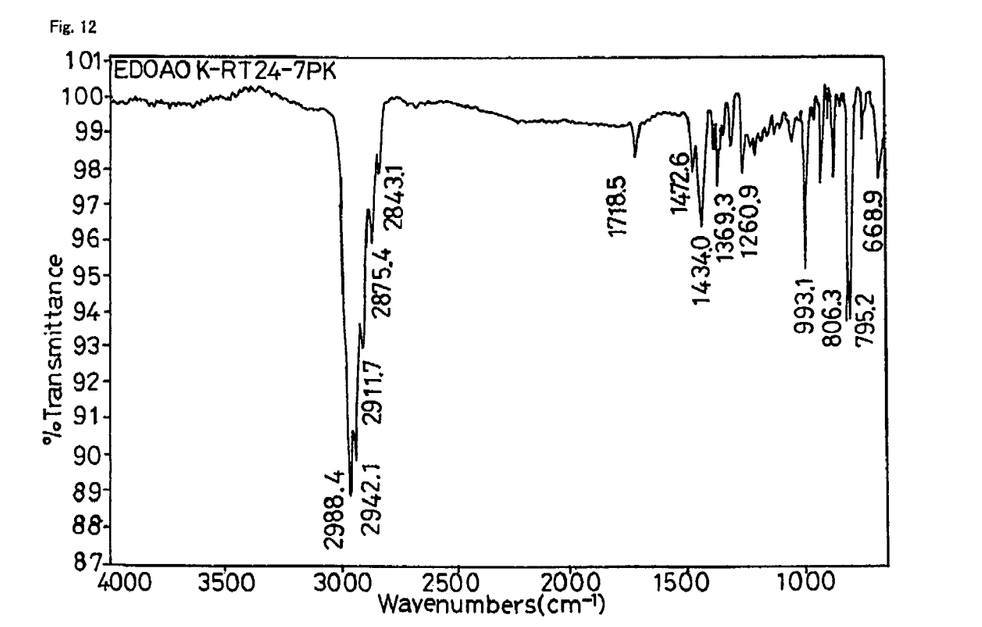
FIG. 12 is an IR chart of a peak at 30.9 minutes observed in the cycloaliphatic diepoxy compound prepared according to Example 1.
Figure 13:
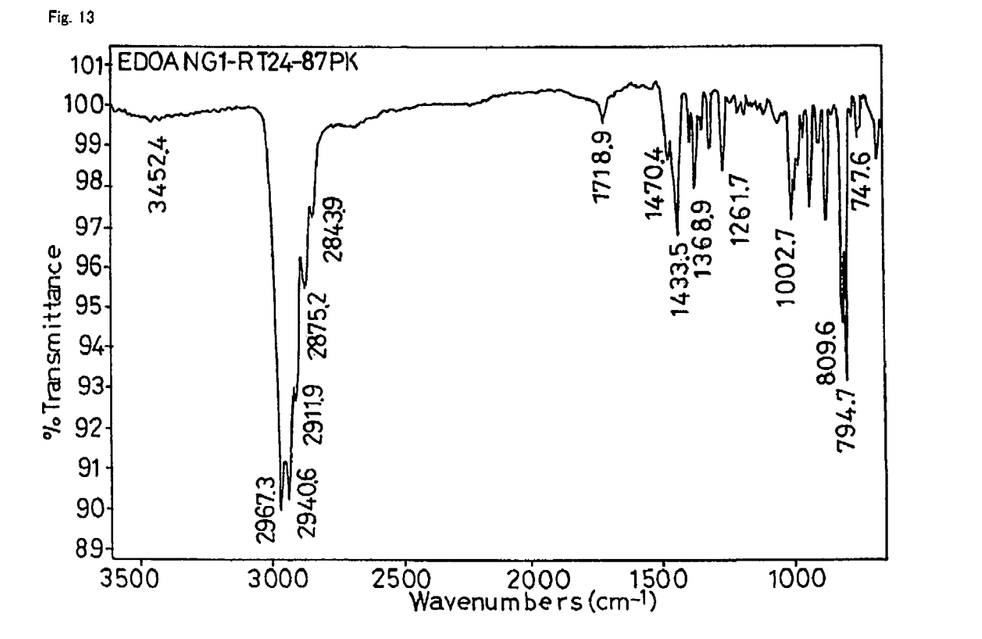
FIG. 13 is an IR chart of a peak at 31.0 minutes observed in the cycloaliphatic diepoxy compound prepared according to Example 1.

IR charts of respective peaks are shown in FIGS. 5 to 7.

Comparative Synthesis Example 1

Synthesis of 2,2-bis(3'-cyclohexenyl)propane

In a 15-liter four-neck flask equipped with a stirrer, a thermometer, and a DEAN-STARK extractor with a Dimroth condenser on its top were placed 6 kg of hydrogenated bisphenol-A, 490 g of potassium hydrogen sulfate as a catalyst, and 6 kg of Solvesso 150 (Exxon Mobil Corporation) as a solvent, and the inside of reaction system was replaced with nitrogen. The flask was then heated to 140° C. to dissolve hydrogenated bisphenol-A, the stirring of the mixture was started, and a dehydration reaction was carried out at 180° C. Water in an amount corresponding to 89% of the theoretical value distilled over nine hours, and the reaction was completed after observing that distillation of water finished.

The organic layer was rectified under reduced pressure and thereby yielded 3830 g of 2,2-bis(3'-cyclohexenyl)propane as a colorless, transparent liquid.

Figure 2:
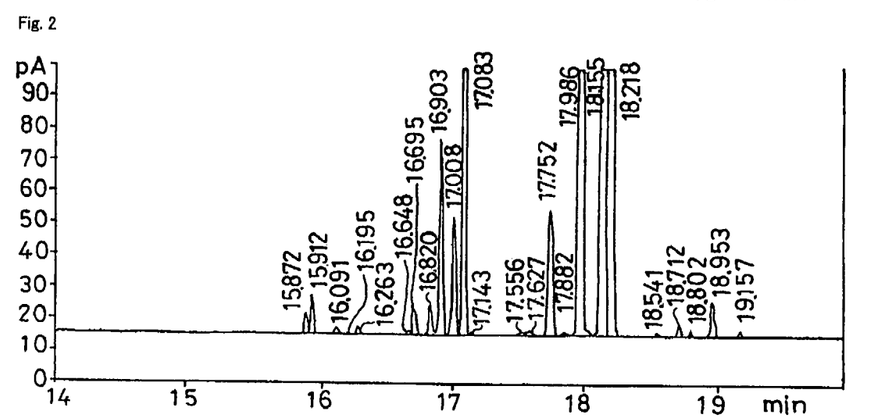
FIG. 2 is a chart in gas chromatograph analysis of 2,2-bis (3'-cyclohexenyl)propane prepared according to Comparative Synthesis Example 1.

The purity of the rectified product was determined by gas chromatograph (according to Gas Chromatograph Analysis 2) to find that the content of 2,2-bis(3'-cyclohexenyl)propane was 75.1%. The chart obtained in the gas chromatograph analysis is shown in FIG. 2.

These by-products are considered to be isomers formed as a result of repeated addition reactions and dehydration reactions between double bonds and water remained in the reaction mixture, which double bonds have been formed as a result of dehydration reaction. The product had an iodine number of 237 ($I_2$-g/100 g) and an APHA of 50.

Preparation Example 1

Compressed air was blown into a 300-ml stainless steel reactor equipped with an air inlet, a gas dispersing perforated plate, and a cooling jacket while feeding a 10% acetaldehyde solution in ethyl acetate containing cobalt acetate at a rate of 114 kg/hour, to carry out a reaction at 45° C. The reaction mixture contained 10.2% of peracetic acid, 2.1% of acetaldehyde monoperacetate, and 2.1% of acetic acid. This solution was placed in a distillation column together with sodium polyphosphate, was concentrated, and thereby yielded a solution of peracetic acid. The peracetic acid solution had a peracetic acid concentration of 29.2% and a water content of 0.31%.

Example 1

In a 1-liter flask with a jacket as above were placed 100 g of 2,2-bis(3',4'-cyclohexenyl)propane prepared according to Synthesis Example 1 and purified thereafter, and 300 g of ethyl acetate. While blowing nitrogen into the gaseous phase, 307.2 g of the solution of peracetic acid in ethyl acetate prepared according to Preparation Example 1 was added dropwise over about two hours so as to maintain the temperature within the reaction system at 30° C. The peracetic acid solution contained substantially no water and had a peracetic acid concentration of 29.2% and a water content of 0.31%. After the completion of the dropwise addition of peracetic acid, the reaction mixture was aged at 30° C. for three hours, and the reaction was completed. The reaction mixture after the completion of reaction was further washed with water at 30° C., from which low-boiling components were removed at 70° C. and 20 Torr. Thereafter, distillation was conducted at a heating temperature of 180° C. and a pressure of 4 Torr using a wiped film evaporator (WFE), to yield 71.2 g of an epoxy compound (A1).

The resulting epoxy compound (A1) had an oxirane oxygen concentration of 12.4%, a viscosity of 1,760 cP (25° C.), and color (APHA) of 15. The $^1$H NMR analysis of this compound demonstrates that a peak at δ of about 4.5 to 5 ppm derived from internal double bond substantially disappears and that a peak of proton derived from epoxy group occurs at δ of about 2.9 to about 3.1 ppm. The target compound herein is a cycloaliphatic diepoxy compound represented by General Formula (II) wherein X is —C(CH$_3$)$_2$—, and each of R$^1$ to R$^{18}$ is hydrogen (H). The produced epoxy compound had a concentration of high-molecular weight components having elution times shorter than that of the target compound as detected in GPC analysis of 5.1%, a concentration of impurities having retention times shorter than that of the cycloaliphatic diepoxy compound as detected in Gas Chromatograph Analysis 1 of 12.1%, and a concentration of reaction intermediates of 2.3%.

Figure 3:
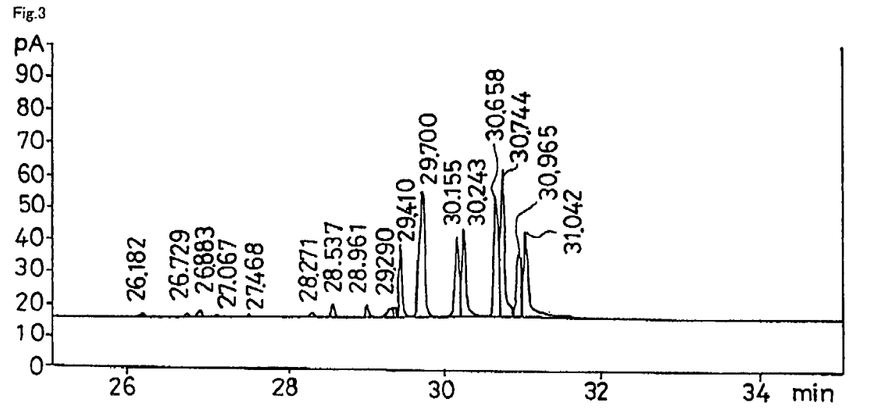
FIG. 3 is a chart in gas chromatograph analysis of a cycloaliphatic diepoxy compound prepared according to Example 1.

The analysis according to Gas Chromatograph Analysis 2 shows that the areal percentage of a main peak observed at retention times of 30.0 minutes to 31.5 minutes was 67.15%. The chart obtained in Gas Chromatograph Analysis 2 is shown in FIG. 3.

IR charts of individual peaks are shown in FIGS. 8 to 13.

Comparative Example 1

There were placed 100 g of 2,2-bis(3',4'-cyclohexenyl) propane prepared according to Comparative Synthesis Example 1 and 300 g of ethyl acetate. While blowing nitrogen into the gaseous phase, 307.2 g of the solution of peracetic acid in ethyl acetate prepared according to Preparation Example 1 was added dropwise over about two hours so as to maintain the temperature inside the reaction system at 30° C. The peracetic acid solution contained substantially no water and had a peracetic acid concentration of 29.2% and a water content of 0.31%. After the completion of the dropwise addition of peracetic acid, the reaction mixture was aged at 30° C. for three hours, and the reaction was completed. The reaction mixture after the completion of reaction was further washed with water at 30° C., from which low-boiling components were removed at 70° C. and 20 Torr. Thereafter, distillation was conducted at a heating temperature of 180° C. and a pressure of 4 Torr using a wiped film evaporator (WFE), to yield 72.7 g of an epoxy compound (A2).

The resulting epoxy compound (A2) had an oxirane oxygen concentration of 12.3%, a viscosity of 2,350 cP (25° C.), and color (APHA) of 20, and the $^1$H NMR analysis thereof demonstrates that a peak at δ of about 4.5 to 5 ppm derived from internal double bond substantially disappears and that a peak of proton derived from epoxy group occurs at δ of about 2.9 to 3.1 ppm. The target compound herein is a cycloaliphatic diepoxy compound represented by General Formula (II) wherein X is —C(CH$_3$)$_2$—, and each of R$^1$ to R$^{18}$ is hydrogen (H). The produced epoxy compound had a concentration of high-molecular weight components having elution times shorter than that of the target compound as detected in GPC analysis of 7.5%, a concentration of impurities having retention times shorter than that of the cycloaliphatic diepoxy compound of 11.9%, and a concentration of reaction intermediates of 2.0%, as detected in Gas Chromatograph Analysis 1.

Figure 4:
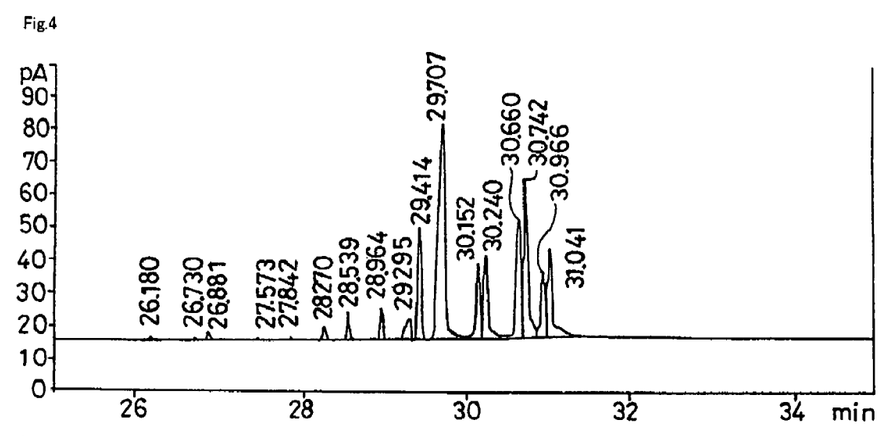
FIG. 4 is a chart in gas chromatograph analysis of a cycloaliphatic diepoxy compound prepared according to Comparative Example 1.

The analysis according to Gas Chromatograph Analysis 2 shows that the areal percentage of a main peak observed at retention times of 30.0 minutes to 31.5 minutes was 54.85%. The chart obtained in Gas Chromatograph Analysis 2 is shown in FIG. 4. IR charts of individual peaks at retention times of 30.1 minutes to 31.0 minutes are shown in FIGS. 8 to 13.

Gelation times of the epoxy compounds (A1) and (A2) prepared according to Example 1 and Comparative Example 1, respectively, were determined. The determination methods and results are shown in Table 1.

[Table 1]

TABLE 1

Comparison in gelation time between epoxy resins

| | Example 1 | Comparative Example 1 |
|---|---|---|
| Gelation Time 1 (sec) | 1241 | 1473 |
| Gelation Time 2 (sec) | 3587 | 4398 |

Gelation Time 1

With 100 parts by weight of a sample epoxy resin was mixed 0.5 part by weight of a curing catalyst (SI-100L, Sanshin Chemical Industry Co., Ltd.), and a gelation time at 80° C. was determined for comparison.

As a gelation point, the time for the resonance frequency of a scanning vibrating needle curing tester (PAPRA Technology Ltd.) to be 100 Hz was used.

Gelation Time 2

With 100 parts by weight of a sample epoxy resin were mixed 129.2 parts by weight of a curing agent (MH-700, New Japan Chemical Co., Ltd.), 1.0 part by weight of ethylene glycol, and 0.5 part by weight of a curing accelerator (triphenylphosphine), and the gelation time at 120° C. was determined for comparison using the same apparatus as in the determination of Gelation Time 1.

INDUSTRIAL APPLICABILITY

High-purity cycloaliphatic diepoxy compounds according to the present invention are useful in applications requiring thermal stability and/or optical transparency, such as coatings, inks, adhesives, sealants, stabilizers, insulating materials, and liquid crystals and other display materials.

The invention claimed is:
1. A process for preparing a high-purity cycloaliphatic diepoxy compound represented by the following Formula (II), the process comprising the steps of:
   purifying a cycloaliphatic diolefinic compound represented by the following Formula (I) through distillation;
   epoxidizing the purified cycloaliphatic diolefinic compound with an aliphatic percarboxylic acid containing substantially no water;
   carrying out desolvation of the epoxidized compound, and further secondarily purifying the epoxidized compound through distillation:

[Chemical Formula 1]

(I)

(II)

wherein X represents a bivalent group selected from the group consisting of an oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ may be the same as or different from each other and each represents a hydrogen atom, a halogen atom, a hydrocarbon group which may contain oxygen atom or a halogen atom, or an alkoxy group which may be substituted.

2. The process for preparing a high-purity cycloaliphatic diepoxy compound according to claim 1, wherein the cycloaliphatic diepoxy compound has a concentration of a reaction intermediate represented by the following Formula (III) and detected in GC analysis of 4.5% or less:

(III)

wherein X represents a bivalent group selected from the group consisting of oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{17}$, and R$^{18}$ may be the same as or different from each other and each represents a hydrogen atom, a halogen atom, a hydrocarbon group which may contain oxygen atom or a halogen atom, or an alkoxy group which may be substituted.

3. The process for preparing a high-purity cycloaliphatic diepoxy compound according to claim 1, further comprising preparing the aliphatic percarboxylic acid through oxidation of a corresponding aldehyde with oxygen.

4. The process for preparing a high-purity cycloaliphatic diepoxy compound according to claim 1, wherein the aliphatic percarboxylic acid has a water content of 0.8 percent by weight or less.

5. The process for preparing a high-purity cycloaliphatic diepoxy compound according to claim 1, wherein the aliphatic percarboxylic acid is peracetic acid.

6. The process for preparing a high-purity cycloaliphatic diepoxy compound according to claim 1, wherein the second purification through distillation is carried out at a heating temperature of 100° C. to 350° C. and a pressure of 50 to 0.01 Torr.

7. The process for preparing a high-purity cycloaliphatic diepoxy compound according to claim 1, wherein the second purification through distillation is carried out at a heating temperature of 150° C. to 350° C. and a pressure of 1 to 10 Torr.

8. The process for preparing a high-purity cycloaliphatic diepoxy compound according to claim 1, wherein the second purification through distillation is carried out at a heating temperature of 180° C. and a pressure of 4 Torr.

9. A composition containing high-purity cycloaliphatic diepoxy compounds represented by formula II, as an epoxidized product of a cycloaliphatic diolefinic compound being represented by the formula I, said compound represented by the formula I having a concentration of contaminating isomers of 15% or less, as detected by gas chromatography (hereinafter referred to as GC), wherein the high-purity cycloaliphatic diepoxy compounds are produced by the process according to claim 1

(I)

(II)

10. The composition containing the high-purity cycloaliphatic diepoxy compound according to claim 9, wherein the isomer comprises at least one of the following compounds:

wherein X represents a bivalent group selected from the group consisting of an oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ may be the same as or different from each other and each represents a hydrogen atom, a halogen atom, a hydrocarbon group which may contain oxygen atom or a halogen atom, or an alkoxy group which may be substituted.

11. The composition containing high-purity cycloaliphatic diepoxy compounds according to claim 9, wherein the cycloaliphatic diepoxy compound has a concentration of high-molecular weight components detected in gel permeation chromatography (hereinafter referred to as GPC) analysis of 5.5% or less, the high-molecular weight components eluting earlier than the cycloaliphatic epoxy compound represented by the following Formula (II) in GPC analysis:

wherein X represents a bivalent group selected from the group consisting of an oxygen atom, sulfur atom, —SO—, —SO$_2$—, —CH$_2$—, —C(CH$_3$)$_2$—, —CBr$_2$—, —C(CBr$_3$)$_2$—, and —C(CF$_3$)$_2$—; and R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ may be the same as or different from each other and each represents a hydrogen atom, a halogen atom, a hydrocarbon group which may contain oxygen atom or a halogen atom, or an alkoxy group which may be substituted.

12. The composition containing high-purity cycloaliphatic diepoxy compounds according to claim 9, wherein the cycloaliphatic diepoxy compounds have a concentration of impurities detected in GC analysis of 19.5% or less, the impurities having retention times shorter than that of the cycloaliphatic epoxy compound Formula (II) in GC analysis.

13. The composition containing high-purity cycloaliphatic diepoxy compounds according to claim 9, said composition has color (APHA) of 60 or less.

14. The composition containing high-purity cycloaliphatic diepoxy compound according to claim 9, wherein gelation time has been shortened by 15% or more compared to other cycloaliphatic diepoxy compounds of high purity.

15. A process for curing a composition containing high-purity cycloaliphatic diepoxy compounds produced by the process according to any one of claims 1 or 2-8, comprising mixing the composition with a curing catalyst or hardener.

16. A cured article produced by the process according to claim 15.

* * * * *